United States Patent
Winston et al.

(10) Patent No.: US 6,394,976 B1
(45) Date of Patent: May 28, 2002

(54) CATHETER FOR CONTROLLING THE ADVANCEMENT OF A GUIDE WIRE

(75) Inventors: Thomas R. Winston, Leawood; John M. Neet, Lawrence, both of KS (US); Jeffery White, Trabuco Canyon, CA (US); John Wardle, San Clemente, CA (US); Diego D. Cueto, Laguna Niguel, CA (US)

(73) Assignee: IntraLuminal Therapeutics, Inc., Carlsbad, CA (US)

( * ) Notice: Subject to any disclaimer, the term of this patent is extended or adjusted under 35 U.S.C. 154(b) by 0 days.

(21) Appl. No.: 09/495,203

(22) Filed: Jan. 31, 2000

(51) Int. Cl.$^7$ ............................................. A61M 37/00
(52) U.S. Cl. ................................................. 604/95.04
(58) Field of Search ............... 604/95.01, 95.04–95.05, 604/523, 264, 528–529

(56) References Cited

U.S. PATENT DOCUMENTS

| | | | |
|---|---|---|---|
| 3,625,200 A | * 12/1971 | Muller | |
| 3,892,228 A | 7/1975 | Mitsui | |
| 5,243,997 A | 9/1993 | Uflacker et al. | |
| 5,308,324 A | * 5/1994 | Hammerslag et al. | ... 604/95.01 |
| 5,346,498 A | 9/1994 | Greelis et al. | |
| 5,383,852 A | * 1/1995 | Stevens-Wright | ........ 604/95.01 |
| 5,456,664 A | * 10/1995 | Heinzelman et al. | .... 604/95.01 |
| 5,499,632 A | 3/1996 | Hill, III et al. | |
| 5,549,119 A | 8/1996 | Solar | |
| 5,702,433 A | * 12/1997 | Taylor et al. | ................ 607/101 |
| 5,810,012 A | 9/1998 | Lynch et al. | |
| 5,904,667 A | 5/1999 | Falwell | |
| 6,035,224 A | * 3/2000 | West | ........................... 600/373 |

* cited by examiner

Primary Examiner—Angela D. Sykes
Assistant Examiner—LoAn H. Thanh
(74) Attorney, Agent, or Firm—Armstrong Teasdale LLP (57) ABSTRACT

A catheter for controlling the advancement of a guide wire includes a catheter body having a central lumen, a first side lumen and a second side lumen. A pair of opposing control wires extend the length of the catheter body through the side lumens. The catheter body includes a proximal portion coupled to a less rigid distal portion. A control handle coupled to the proximal ends of the control wires produces opposing motion of the control wires along the length of the catheter body, causing the distal portion of the catheter body to deflect relative to the proximal portion of the catheter body, thus directing the guide wire. In one embodiment, the control handle includes a guide wire advancement mechanism for controlling the advancement of the guide wire through the catheter.

28 Claims, 7 Drawing Sheets

CATHETER FOR CONTROLLING THE ADVANCEMENT OF A GUIDE WIRE

BACKGROUND OF THE INVENTION

This invention relates generally to medical instruments and, more particularly, to systems and methods for controlling the advancement of a guide wire through a body or a portion of the body, such as a blood vessel.

Guide wires are used during various interventional medical procedures to navigate therapeutic devices to a treatment site within a body, such as within a blood vessel. For example, to use a PTCA balloon device to clear an obstruction from a coronary artery, a guide wire is inserted into the femoral artery and advanced through the aorta to the obstruction in the coronary artery. The PTCA balloon device is then introduced over the wire and guided by the guide wire to the obstruction, where the balloon is then used to clear the obstruction.

However, advancing and steering guide wires through blood vessels is a difficult and risky procedure, even when practiced by skilled operators. Vessels are often tortuous or obstructed, or the tip of the guide wire itself is difficult to control. Thus, the use of guide wires typically entails the risk of puncturing or damaging the blood vessel, or else the guide wire simply fails because it is not rigid enough to penetrate certain barriers such as arterial plaque. A total occlusion of a blood vessel is an especially challenging barrier to successful use of a guide wire. Often, such occlusions are hardened by calcification and thus especially difficult to penetrate with a guide wire. When the tip of a guide wire is forced against such a hardened occlusion, the tip may be deflected toward the blood vessel wall, and, if advanced, may perforate the wall. To avoid such an undesirable outcome, the guide wire must be manually advanced by a skilled operator in carefully controlled increments. However, this is a difficult skill to acquire and even the most highly skilled operators risk damaging vessel walls. In addition, some calcified lesions present impenetrable barriers to the guide wire, even when operated by the most highly skilled operators.

A total occlusion of a blood vessel is an especially challenging barrier to successful use of a guide wire. Often, such occlusions are hardened by calcification and thus especially difficult to penetrate with a guide wire. When the tip of a guide wire is forced against such a hardened occlusion, the tip may be deflected toward the blood vessel wall, and, if advanced, may perforate the wall. To avoid such an undesirable outcome, the guide wire must be manually advanced by a skilled operator in carefully controlled increments. However, this is a difficult skill to acquire and even the most highly skilled operators risk damaging vessel walls. In addition, some calcified lesions present impenetrable barriers to the guide wire, even when operated by the most highly skilled operators.

Known guide wires include wires which range in diameter from 0.010 inches to 0.050 inches, and range in length from 2 feet to 10 feet. The distal tip of a typical known guide wire is shapeable into a curved or bent configuration and steered by turning the wire at the proximal end, thus transmitting torque through the wire to the distal tip. Known wires have varying degrees of rigidity (stiffness) which are selected according to the requirements of the particular procedure being performed. Softer, floppier wires are less likely to perforate vessel walls and are therefore better for navigating through tortuous arteries, but softer wires do not readily penetrate and cross occlusions. Stiffer wires are better for penetrating occlusions, but carry a greater risk of perforating or damaging vessel walls. Thus, an operator must trade off stiffness against a higher risk of perforation.

Other known guiding devices include catheters having a lumen for accommodating the movement of a guide wire. Such catheters are usually used in combination with a therapeutic device such as a PTCA balloon catheter. Known catheters also include exchange catheters, such as the Buchbinder catheter, which hold a position in the body while a wire extending through the catheter lumen is removed and replaced with a different wire. However, such catheters do not steer a guide wire through tortuous tissue, and do not provide incremental control of guide wire advancement to minimize risk of damage.

It would therefore be desirable to provide a catheter for controlling the advancement of a guide wire, wherein the catheter has a distal tip that can be deflected or steered so that the advancement of the guide wire inside a vessel can be more carefully controlled. It would also be desirable to provide such a catheter that controls the incremental forward movement of the guide wire distal tip. It would be further desirable to provide such a catheter coupled to an energy source to facilitate penetration of the catheter distal tip through difficult tissue such as total occlusions. It would be yet still further desirable to provide a catheter with a distal tip which can be stiffened as needed to penetrate occlusions, but which can also be allowed to soften to allow to facilitate steering through vessels.

BRIEF SUMMARY OF THE INVENTION

These and other objects are attained by a catheter for controlling the advancement of a guide wire. In one embodiment the catheter includes a catheter body having a proximal end and a distal end, a first side lumen and a second side lumen, and a central lumen. A first control wire extends through the first side lumen, and a second control wire extends through the second side lumen. In one embodiment, the control wires each have a distal end that is coupled to the distal end of the catheter body. The catheter body includes a first, proximal portion and a second, distal portion. The distal portion is more flexible than the first portion so that the distal portion of the catheter body is flexible through a plurality of positions relative to the base portion. A control handle is coupled to the proximal end of the proximal catheter body portion. The control handle includes a control knob coupled to a deflection mechanism, which is coupled to the proximal ends of the control wires. The deflection mechanism translates movement of the control knob to motion of the control wires such that the wires move in opposing directions along the length of the catheter body. Thus, movement of the control knob produces opposing forces of the control wires on the distal portion of the catheter body, thereby causing the distal portion to flex relative to the first, proximal portion.

In an alternate embodiment, the first and second control wires are instead a first control portion and a second control portion of a single continuous control wire. An end of the single wire is introduced into the first side lumen at the proximal end, looped around at the distal end of the catheter body, and re-introduced into the catheter, into the second side lumen, terminating at the proximal end.

The present invention further includes a guide wire advancement mechanism in the control handle for controlling the advancement of a guide wire inserted through the catheter. The control handle knob is coupled to the advancement mechanism. The advancement mechanism includes a spring assembly in reversible engagement with a friction wheel. The guide wire passes through a guiding channel in a spring block in the spring assembly, so that the guide wire reversibly makes contact with the friction wheel. A geared drive wheel is coupled to the friction wheel. A first ratchet element coupled to a first spring element on the control handle housing reversibly engages the gear teeth on the drive wheel. "Clicking" or brief pressure on the control knob engages the first spring element and first ratchet element so that the first ratchet element "clicks" forward one tooth on the geared drive wheel, thus rolling friction wheel forward. The guide wire making contact with the friction wheel is thus advanced incrementally forward. In one embodiment, a second ratchet element in engagement with a second geared drive wheel provides a brake against further advancement of the guide wire. In another aspect, the present invention is directed toward a catheter that navigates through difficult tissue by using an energy source to impart vibrational or rotating movement to tubing coupled to the catheter distal end. The energy source is coupled to the tubing by a PZT crystal, a rotating cam or a speedometer type cable.

DETAILED DESCRIPTION OF THE INVENTION

Figure 1:
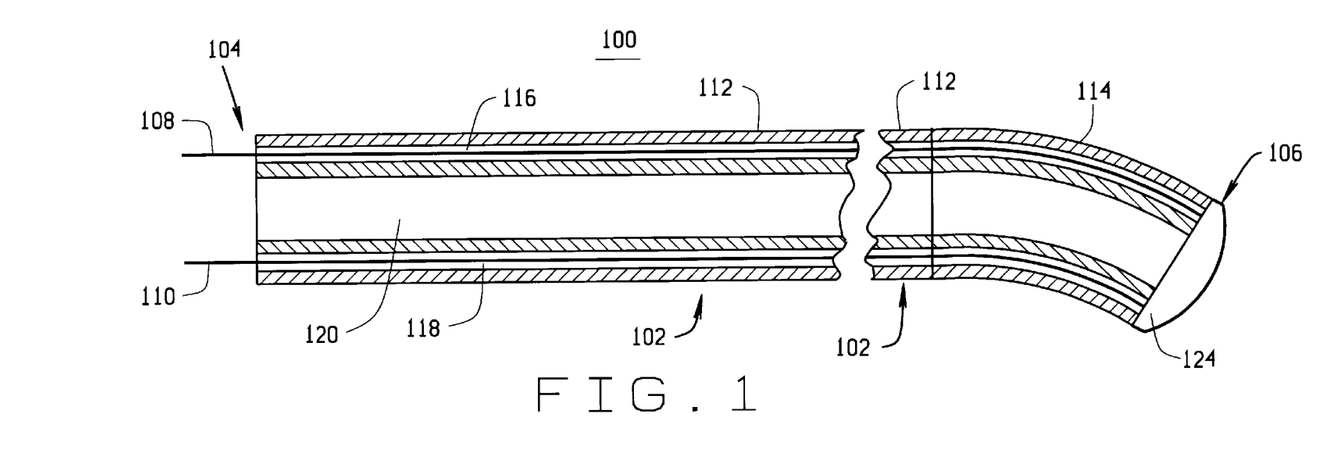
FIG. 1 is a first side cross-sectional view of a control catheter.

FIG. 1 is a first side cross-sectional view of an exemplary embodiment of a catheter 100. In the one embodiment, catheter 100 includes a main catheter body 102 having a proximal end 104 and a distal end 106. A pair of opposing control wires 108 and 110 extends along the length of catheter body 102. Catheter body 102 includes a first, proximal portion 112 and a second, distal portion 114, wherein distal portion 114 is fabricated from a material that is less rigid than the first portion. Thus, distal portion 114 is flexible through a plurality of positions relative to proximal portion 112. As described in more detail below, a control handle is coupled to proximal end 104. The control handle includes a control knob coupled to a deflection mechanism as described below, which is coupled to the proximal ends of the control wires 108 and 110. Movement of the control knob is translated by the deflection mechanism to motion of wires 108 and 110 such that the wires move in opposing directions along the length of catheter body 102. Thus, movement of the control knob produces opposing forces of the control wires on the distal portion of the catheter body, thereby causing distal portion 114 to flex relative to first, proximal portion 112.

Catheter body 102 is fabricated from extruded thermal plastic tubing having multiple lumens therethrough. In one embodiment, catheter body 102 has two side lumens 116 and 118, lumen 116 for accommodating control wire 108 and lumen 118 for accommodating control wire 110, and a central lumen 120 for accommodating a guide wire or other device. Lumens 116 and 118 extend along the length of catheter body 102 in diametrically opposed position to one another. In alternative embodiments, catheter 100 has more than one central lumen 120, for example two or three central lumens, in addition to side lumens 116 and 118. The number of central lumens in catheter body 102 is determined according to the intended use of catheter 102.

Both catheter body proximal portion 112 and distal portion 114 are fabricated from extruded thermal plastic tubing, but distal portion 114 is fabricated from material which is less rigid or softer than the material used for proximal portion 112. Thus, distal portion 114 is deflectable relative to proximal portion 112. For example, in one embodiment proximal portion 112 is fabricated from 60 to 100 Shore D durometer tubing, and distal portion 114 is fabricated from 25 to 50 Shore D tubing. Distal portion 114 is bonded to proximal portion by adhesive, ultrasonic welding or thermal bonding.

In an alternative embodiment, distal portion 114 is fabricated from material including a radio-opaque marker such as, for example, barium sulfate, so that distal portion 14 is radio-opaque for ready visualization under x-ray imaging. In other alternative embodiments, conventional marking schemes such as banding are used to mark distal portion 114 to facilitate visualization under x-ray imaging.

Figure 2:
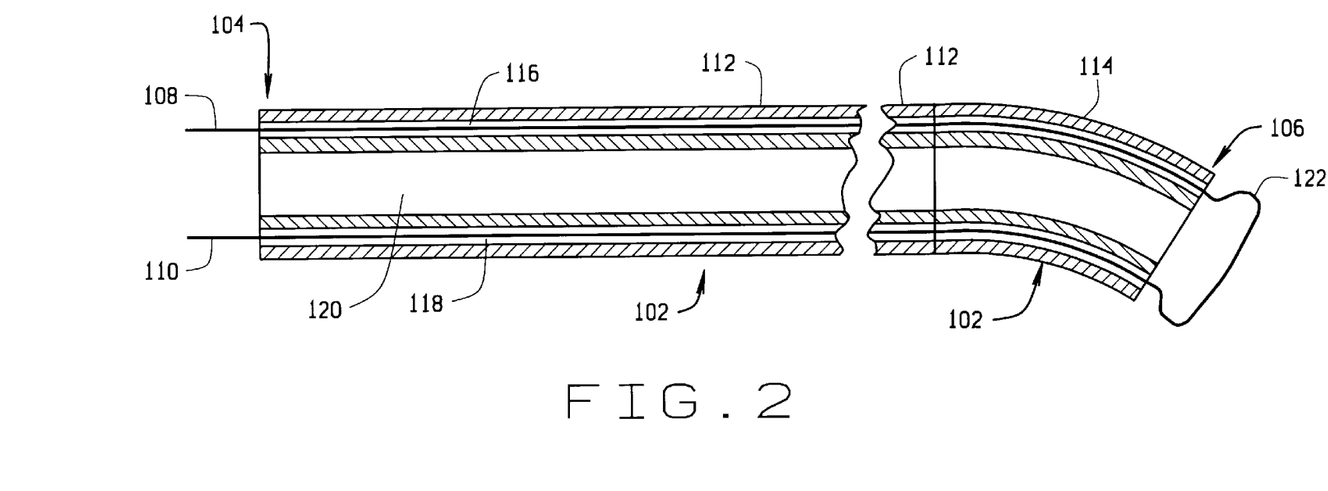
FIG. 2 is a second side cross-sectional view of the catheter.

FIG. 2 shows a second side cross-sectional view of an exemplary embodiment of catheter 100. In this embodiment, control wires 108 and 110 are not separate pieces of wire but instead two portions of one continuous wire. The single wire is introduced, for example, into lumen 116 at proximal end 104, pushed through body 102 and out distal end 106, then re-introduced into opposing lumen 118 at distal end 106 and reverse fed through lumen 118 until the wire is pulled back out proximal end 104. At catheter distal end 106, the wire forms a loop 122. Loop 122 is pulled sufficiently tight to a semicircular shape that lies flat against distal end 106 of catheter body 102. In an alternative embodiment, control wires 108 and 10 are separate wires each having a distal end. The distal end of each wire is coupled to distal end 106 of catheter body 102.

Suitable material for fabricating control wires 108 and 110 is any strong, yet kink-resistant material, such as stainless steel wire, braids or cables. In one exemplary embodiment, nitinol wire is used for control wires 108 and 110 and is especially suitable because of its super-elastic properties.

Figure 3:
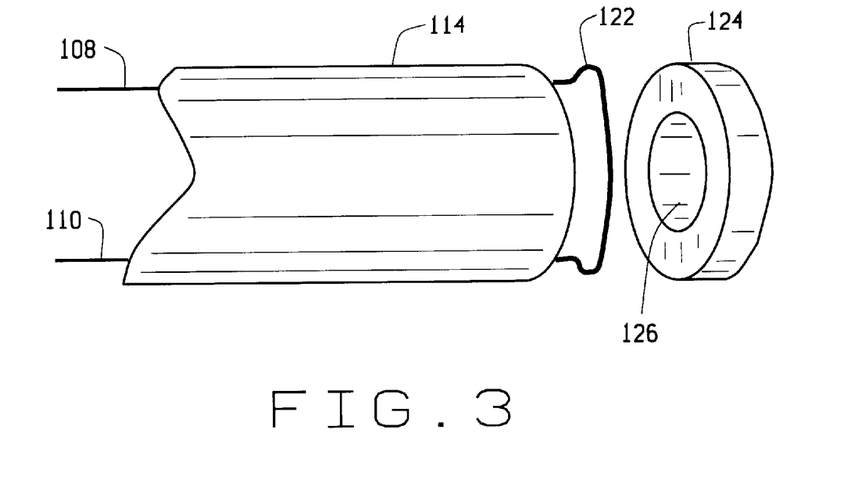
FIG. 3 is a perspective view of the catheter distal end.

FIG. 3 is a perspective view of catheter distal end 106. In one embodiment, distal end 106 is capped with a cap 124 fabricated from the same material as that used for distal portion 114. Cap 124 has a central opening 126 therethrough having a diameter approximately the same as the diameter of central lumen 120. Cap 124 is bonded to distal portion 114 for example by thermal bonding, adhesive or ultrasonic welding. Cap 124 thus fixes or entraps loop 122 in a fixed position at distal end 106. In one embodiment, cap 124 is marked with a radio-opaque marker as described above, for visualization under x-ray imaging.

Figure 4:
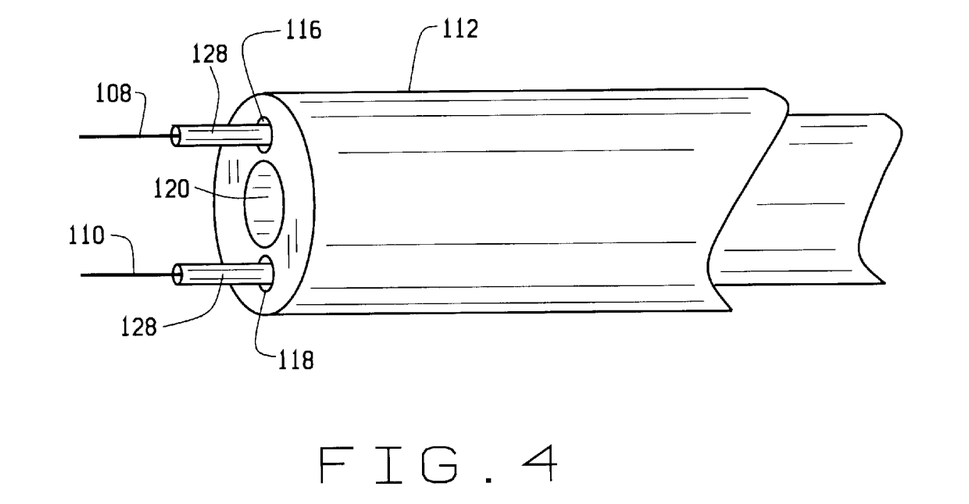
FIG. 4 is a perspective view of the catheter proximal end.

FIG. 4 is a perspective view of catheter proximal end 104, showing first side lumen 116, second side lumen 118 and central lumen 120. In one embodiment, lumens 116 and 118 are reinforced with hypodermic tubing 128 to facilitate the sliding movement of control wires 108 and 110 within lumens 116 and 118, and to improve the strength and torqueability of catheter 100. For example, with control wires 108 and 110 of 0.005" (inches) wire, suitable material for tubing 128 is hypodermic tubing having an inner diameter of 0.006" and an outer diameter of 0.010". Of course, the diameter of tubing used for reinforcing lumens 116 and 118 will vary depending on the diameter of wire used for control wires 108 and 110, which itself can also vary. In an alternative embodiment, the lumens 116, 118 and 120 are left unreinforced, with no hypodermic tubing.

Figure 5:
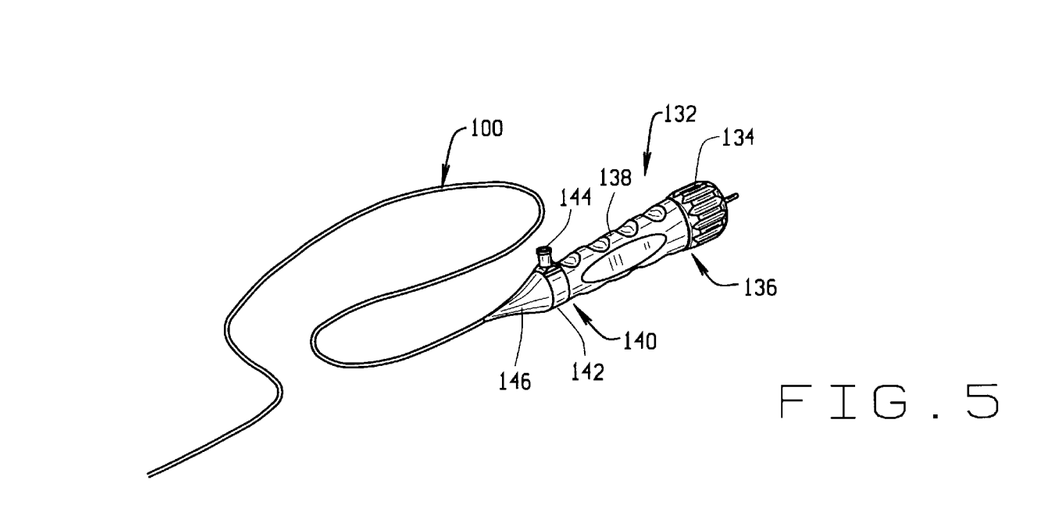
FIG. 5 is a perspective view of a control handle coupled to the catheter proximal end.

FIG. 5 is a perspective view of a control handle 132 coupled to catheter 100. More specifically, control handle 132 is coupled to proximal end 104 of catheter body 102. Control handle 132 includes a rotatable control knob 134 or thumb wheel coupled to a first, proximal end 136 of a housing 138. Coupled to a distal end 140 of housing 138 is a rotating flush port 142, which includes a port connector 144 for coupling handle 132 to, for example, a flushing catheter. Coupled to flush port 142 is a strain relief 146 having an opening 148 (not shown in FIG. 5) therethrough, through which proximal end 104 of catheter 100 is inserted. In one embodiment, strain relief 146 is fabricated from a flexible material such as a rubber, rubber composite or flexible plastic.

Figure 6:
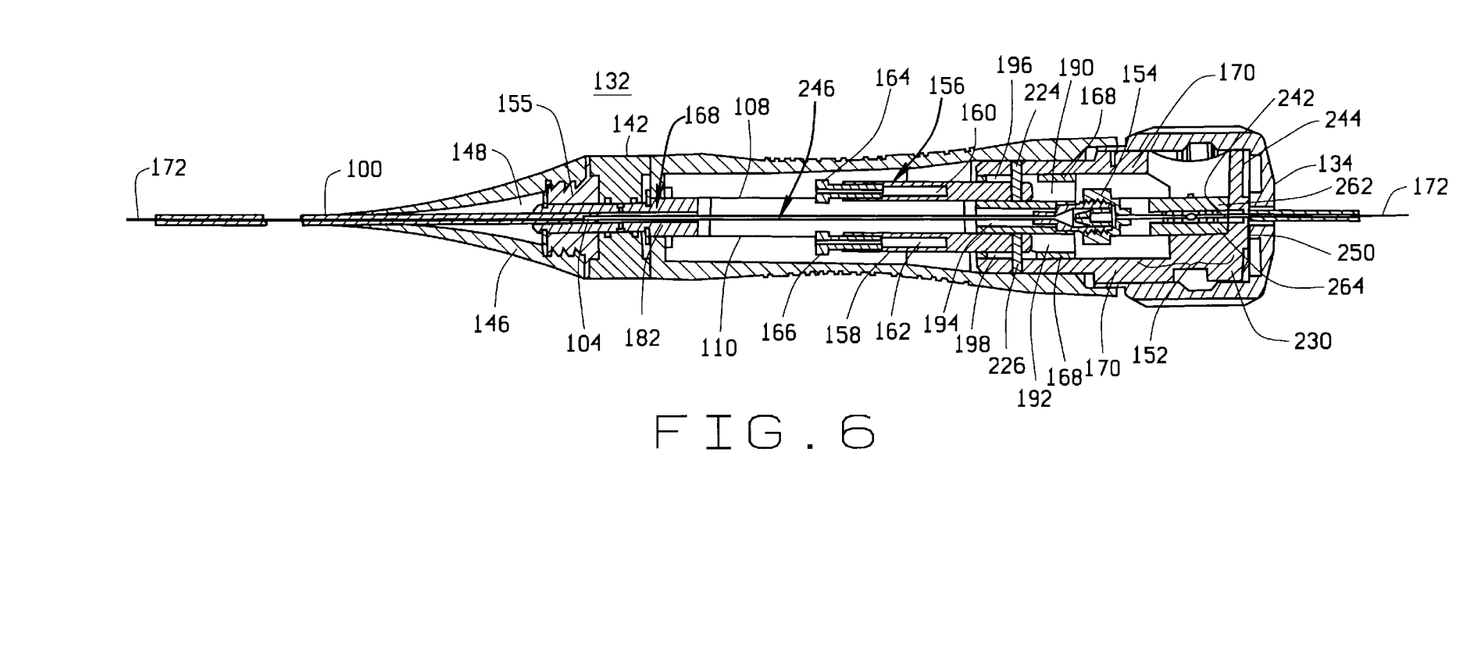
FIG. 6 is a top cross-sectional view of the control handle.

FIG. 6 is a top cross-sectional view of control handle 132. Control handle 132 includes, within control knob 134 and housing 138, a deflection mechanism 150 for deflecting catheter 100, and a guide wire advancement mechanism 152 for controlling the advancement of a guide wire (not shown) inserted through catheter 100. In an exemplary embodiment, control knob 134 is coupled to deflection mechanism 150 so that rotation of control knob 134 results in deflection of catheter 100. As explained in detail below, control knob 134 is also coupled to advancement mechanism 152 so that manual pushing or clicking on control knob 134 controls advancement of a guide wire extending through catheter 100. Control handle 132 further includes a valve assembly 154 for preventing fluid from backing up catheter 100 and leaking through catheter handle 132. Strain relief 146 includes a bushing 155 having an opening therethrough. Proximal end 104 of catheter 100 inserts through strain relief 146, through the opening in bushing 155, and is bonded to deflection mechanism 150 as described in detail below.

In one embodiment, deflection mechanism 150 extends through housing 138 from control knob 134 to strain relief 146. In one embodiment, deflection mechanism 150 includes a yoked assembly coupled to control wires 108 and 110, and further coupled to control knob 134. The yoked assembly is configured so that rotation of control knob 134 translates to motion of wires 108 and 110 such that the wires move in opposing directions along the length of catheter 100, thus producing deflection of catheter 100. In an exemplary embodiment, the yoked assembly includes a first guide pin 156 and a second guide pin 158. Guide pins 156 and 158 are substantially identical, each having a threaded hollow chamber 160 and 162 respectively, into which the proximal ends of control wires 108 and 110 are respectively inserted. Adjustment screws 164 and 166 insert respectively into chambers 160 and 162 and are used to secure the proximal ends of control wires 108 and 110 respectively within hollow chambers 160 and 162. The tension on control wires 108 and 110 is adjustable by tightening or loosening adjustment screws 164 and 166.

Deflection mechanism 150 further includes a chassis 168 (shown more clearly in FIGS. 7 and 8) in rotatably sliding engagement with a control cylinder 170. Chassis 168 is, for example, fabricated as a unitary piece from a molded plastic material, and generally defines a first, long axis 172 extending the length of control handle 132 from control knob 134 to strain relief 146. Chassis 168 includes a first, cylindrical portion 174, a first elongate member 176 and a second elongate member 178 extending from cylindrical portion 174, a cross member 180 joining first and second elongate members 176 and 178, and a distal tip portion 182 joined to cross member 180. An opening 184 extends through distal portion 182 and cross member 180, along long axis 172. Proximal end 104 of catheter 100, after passing through strain relief 146 and bushing 155, is bonded to distal tip portion 182 of chassis 168, for example with epoxy adhesive or the like.

Figure 7:
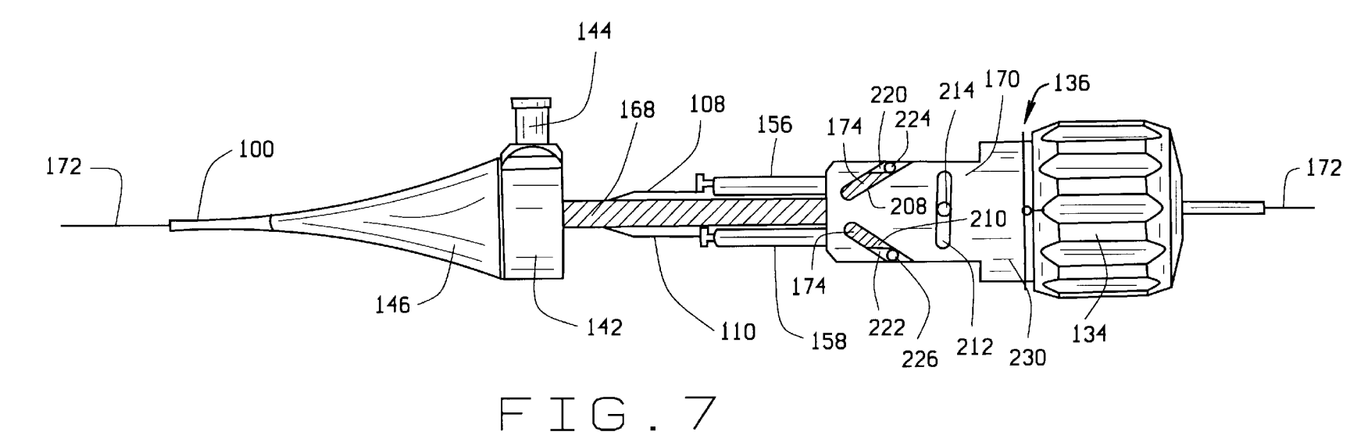
FIG. 7 is a top view of the control handle with an external housing removed.

Cylindrical portion 174 of chassis 168 has a first side bore 190, a second side bore 192, and a central bore 194 therethrough, the bores extending through cylindrical portion 174 along long axis 172. First side bore 190 and second side 192 are located at opposing positions on either side of central bore 194, and are sized so that guide pins 156 and 158 slidably engage within bores 190 and 192, as described in more detail below. Cylindrical portion 174 also has a first side slot 196 therethrough, first side slot 196 extending substantially parallel to long axis 172, in alignment with first side bore 190, and a second side slot 198 therethrough, second side slot 198 extending substantially parallel to long axis 172, in alignment with second side bore 192.

FIG. 7 is a top view of control handle 132 with housing 138 removed. Generally, control cylinder 170 rotatably engages chassis 168. More specifically, control cylinder 170 is coupled to control knob 134, and cylindrical portion 174 of chassis 168 slidably engages a central bore through control cylinder 170. Control cylinder 170 has a first side slot 208 and a second side slot 210 therethrough. First side slot 208 and second side slot 210 are positioned on opposing sides of control cylinder 170, and extend at opposing angles of about 45° with respect to long axis 172. More specifically, for example, when control cylinder 170 is viewed from a first side, first side slot 208 extends at an angle of about 45°, down to the right with respect to long axis 172. When control cylinder is flipped to view the second, opposing side, second side slot 210 extends at an angle of about 45°, up to the right with respect to long axis 172. In one embodiment, control cylinder 170 further includes a third, locking slot 212 therethrough, wherein third slot 212 extends substantially perpendicularly relative to long axis 172, and between first side slot 208 and second side slot 210. A locking pin 214 extends from chassis cylindrical portion 174 and engages third slot 212 to hold control cylinder 170 and and chassis 168 together, while allowing rotation of chassis 168 within the bore of control cylinder 170.

As described above, cylindrical portion 174 of chassis 168 slidably engages the central bore of control cylinder 170. More specifically, cylindrical portion 174 inserts into the central bore of control cylinder 170 so that first side slot 196 of cylindrical portion 174 partly overlaps, or partially aligns, with first side slot 208 of control cylinder 170. Where cylindrical portion first side slot 196 and control cylinder first side slot 208 overlap, a first movable opening 220 is formed, extending through cylindrical portion 174 to first side bore 190 of cylindrical portion 174. Further, second side slot 198 of cylindrical portion 174 partly overlaps with second side slot 210 of control cylinder 170. Where cylindrical portion second side slot 198 and control cylinder second side slot 210 overlap, a second movable opening 222 is formed, extending through cylindrical portion 174 to second side bore 192 of cylindrical portion 174.

The proximal end of first guide pin 156 slidably inserts into first side bore 190 of cylindrical portion 174, and the proximal end of second guide pin 158 slidably inserts into second side bore 192 of cylindrical portion 174. A first dowel pin 224 inserts through first movable opening 220, and into an opening (not shown) in first guide pin 156. A second dowel pin 226 inserts through second movable opening 222, and into an opening (not shown) through second guide pin 158. In an exemplary embodiment, to secure the dowel pins to the guide pins, first dowel pin 224 and second dowel pin 226 have a threaded portion, and the guide pin openings are correspondingly threaded so that the dowel pins are threadedly engaged with the guide pin openings. In alternative embodiments, the dowel pins are secured to the guide pins by, for example, epoxy adhesive, or other mechanical coupling methods.

The positions of dowel pins 224 and 226 are movable, and depend upon the positions of first movable opening 220 and second movable opening 222. The positions of first movable opening 220 and second movable opening 222 vary with the relative positions of control cylinder 170 and cylindrical portion 174 as they are rotated with respect to one another, and the partially overlapping slots change position with respect to one another. As control cylinder 170 and cylindrical portion 174 are rotated with respect to one another, dowel pins 224 and 226 slide along the slots in opposing directions along long axis 172 as the positions of first movable opening 220 and second movable opening 226 correspondingly vary. End knob 134 is coupled to control cylinder 170 so that manual rotation of control knob 134 produces rotation of control cylinder 170. Thus, the opposing movement of guide pins 156 and 158 along long axis 172, wherein dowel pin 156 and 158 are coupled respectively to dowel pins 224 and 226, produces opposing tensile forces on control wires 108 and 110 and corresponding deflection of distal portion 114.

Figure 8:
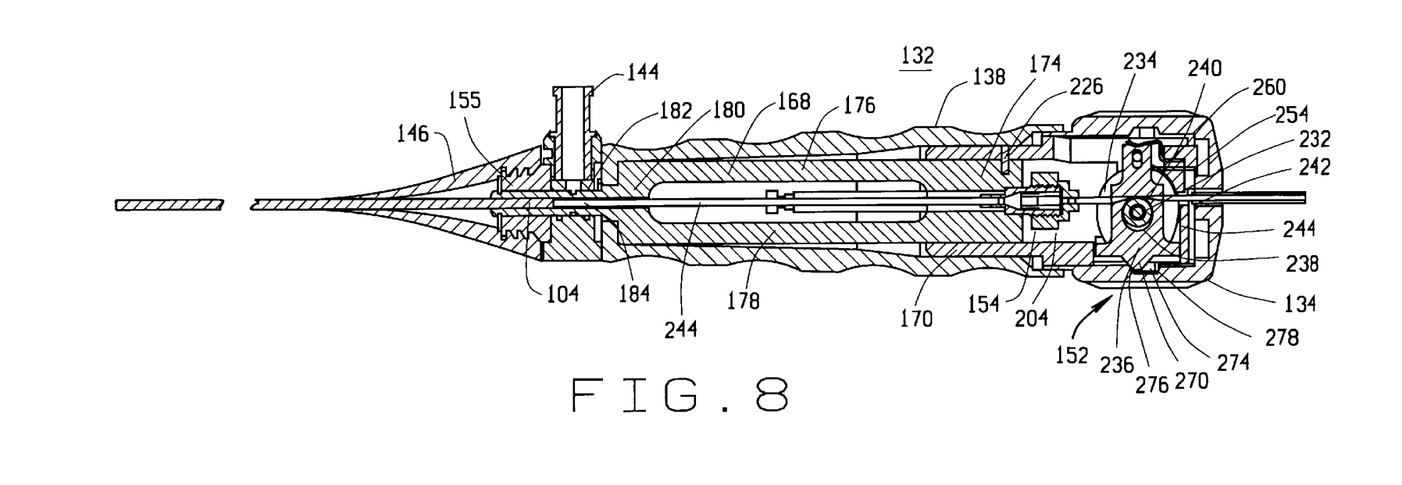
FIG. 8 is a side cross-sectional view of control handle.

FIG. 8 is a side cross-sectional view of control handle 132, showing guide wire advancement mechanism 152 more clearly. Advancement mechanism 152 precisely controls the advancement of a guide wire inserted through central lumen 120 passed through handle 132. If necessary, advancement mechanism 152 imparts reciprocating motion to the guide wire to facilitate penetration of tissue such as calcified plaque. In use, the guide wire extends through housing 138, passing through advancement mechanism 152 and past deflection mechanism 150 before passing into catheter central lumen 120.

Referring to FIGS. 7 and 8, guide wire advancement mechanism 152 is housed within a housing portion 230 of control cylinder 170 that slidably engages within control knob 134. A spring assembly within housing portion 230 includes a friction wheel 232 coupled to a geared drive wheel 234. The spring assembly also includes a spring assembly block 236 having a central opening 238 therethrough, and a guide wire guiding channel 240 extending therethrough. Central opening 238 and channel 240 are continuous. Friction wheel 232 fits within central opening 238. A first portion 242 of hypodermic tubing extends through a central opening 243 (shown in FIG. 9) through control knob 134, through an opening (not shown) in a proximal wall 244 of housing portion 230, and terminates where friction wheel 232 engages central opening 238 of spring assembly block 236. A second portion 246 of hypodermic tubing extends from the spring assembly central opening 238, through an opening (not shown) in a distal wall of housing portion 230, through central bore 194 of cylindrical portion 174. Thus, a guide wire inserted through first portion 242 of hypodermic tubing, and passed through channel 240 to second portion 246 of hypodermic tubing, makes contact with friction wheel 232. Second portion 246 of hypodermic tubing extends along long axis 172 and through chassis 168, between first elongate member 176 and second elongate member 178, through the opening through cross member 180 and through distal tip portion 182 of chassis 168.

A first spring element 250 extends outwardly from proximal wall 244 of housing portion 230. A first ratchet element 254 is coupled to first spring element 250, and extends into housing portion 230 to reversibly engage a tooth of geared drive wheel 234. A second ratchet element (not shown) is anchored to proximal wall 244 of housing portion 230, and also extends into housing portion 230 to slidably engage a tooth of drive wheel 234. In an exemplary embodiment as shown more clearly in FIG. 7, geared drive wheel 234 includes a pair of coupled geared wheels 262 and 264, of identical diameter, wherein spring assembly block 236 is positioned between the paired geared wheels. First ratchet element 254 engages first geared wheel 262, and the second ratchet element engages second geared wheel 264.

Referring again to FIG. 8, a second spring element 260 is anchored to proximal wall 244 above spring assembly block 236, contacting spring assembly block 236 to produce a force against spring assembly block 236. Second spring element 260 thus maintains spring assembly block 236 in a first, braking position as shown in FIG. 8. In the first position, spring assembly block 236 holds friction wheel 232 in contact with a guide wire extending through spring assembly block 236, thus impeding the forward movement of the guide wire through guiding channel 240.

Figure 9:
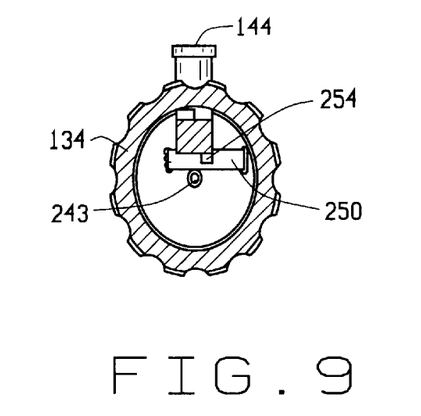
FIG. 9 is a sectional view through a proximal end of the control handle.

FIG. 9 is a sectional view through control knob 134, showing first spring element 250 and first ratchet element 254. In an exemplary embodiment, first ratchet element 254 is a substantially L-shaped metal strip. A first leg of first ratchet element 254 hooks over first spring element 250, while the second leg of ratchet element 254 extends into housing portion 230. Thus, back and forth movement of spring element 250 causes the second leg of first ratchet element 254 to reversibly engage first geared drive wheel 262 as described above.

Opposite the contact of second spring element 260 with spring assembly block 236, spring assembly block 236 includes an angled pedestal 270 in sliding engagement with an inner surface of control knob 134. More specifically, the control knob inner surface defines a depression or indentation 274 with a first distal ramp 276 and a second proximal ramp 278. Pedestal 270 slidably engages indentation 274 so that when control knob 134 is pushed and held inward toward housing 138, pedestal 270 slides up proximal ramp 278, thus forcing spring assembly block 236 against second spring element 260. Thus spring assembly block 236 carries or moves the guide wire in channel 240 away and out of contact with friction wheel 232. Once the guide wire is free of contact with friction wheel, the guide wire is free to move forward. The guide wire can then be advanced forward manually, free of friction wheel 232.

Alternatively, advancement mechanism 152 operates to advance the guide wire in precise, incremental steps. To advance the guide wire forward in precise incremental steps of less than about 0.5 mm, manual pressure is briefly applied to knob 134 by "clicking" knob 134 toward housing 138, against the force produced by first spring element 250, and then releasing knob 134. The pressure against first spring element 250 causes first ratchet element 254 to push against the engaged tooth of first geared wheel 262, and to slide behind the next tooth on the wheel. At the same time, pedestal 270 of spring assembly block 236 is briefly forced up proximal ramp 278 as described above, thereby briefly allowing a brief rotation of friction wheel 232 in a counter-clockwise direction, causing the guide wire to be moved forward. Second ratchet element 258 acts as a locking element against further, undesired rotation of friction wheel 232. The amount of rotation of friction wheel 232 and thus the corresponding forward motion of the guide wire is thus limited by the time it takes for first ratchet element 254 and second ratchet element to engage the next tooth on, respectively, first and second geared wheels 262 and 264. Thus, the guide wire is moved forward in incremental steps controlled by the engagement of the geared drive wheel or wheels by the ratchet elements.

Further, since paired geared drive wheels 262 and 264 are larger than friction wheel 232, the actual forward movement of the guide wire is reduced by the ratio of the friction wheel diameter to the drive wheel diameter, relative to the actual forward movement of knob 134. The amount of advancement per each incremental advancement of the geared drive wheels 262 and 264 can be adjusted by altering the diameter ratio of friction wheel 232 and drive wheels 262 and 264 or by the number of teeth on the drive wheels.

To retract the guide wire, or to move the wire freely in either direction, the operator withdraws or pulls control knob 134 into a locked position, away from handle housing 138, thus relieving pressure on friction wheel 232 and freeing the guide wire. To lock control knob 134 into position, control knob 134 has a groove (not shown) which pedestal 270 engages when control knob 134 is withdrawn. At times, it is advantageous to move the wire in a reciprocating motion to facilitate advancement through difficult tissue, such as a calcified plaque. The reciprocating motion is achieved by introducing movement in control knob 134 as described below. Control knob 134 is moved at increments of about one half the required full step movement so that the wire moves back and forth between advancing steps. This movement is accomplished, for example, with an electromagnetic actuator, a PZT crystal, or a rotating cam. Similarly, in an alternative embodiment, larger reciprocating motion is introduced by imparting reciprocating movement to spring assembly 186, thus moving assembly 186 and the guide wire in combination.

In an alternative embodiment of guide wire advancement mechanism 152, a roller bearing is included within housing 138, in contact with the guide wire extending through guiding channel 240, so that the guide wire moves between friction wheel 232 and the roller bearing. The roller bearing produces a force opposing the force applied to the guide wire by friction wheel 232 when spring assembly block 236 is in the first, braking position. The roller bearing acts to concentrate the frictional force from friction wheel 232 on the guide wire itself, and not on the opposing surface in spring assembly block 236, thus improving the transmission of frictional force to the guide wire.

Figure 10:
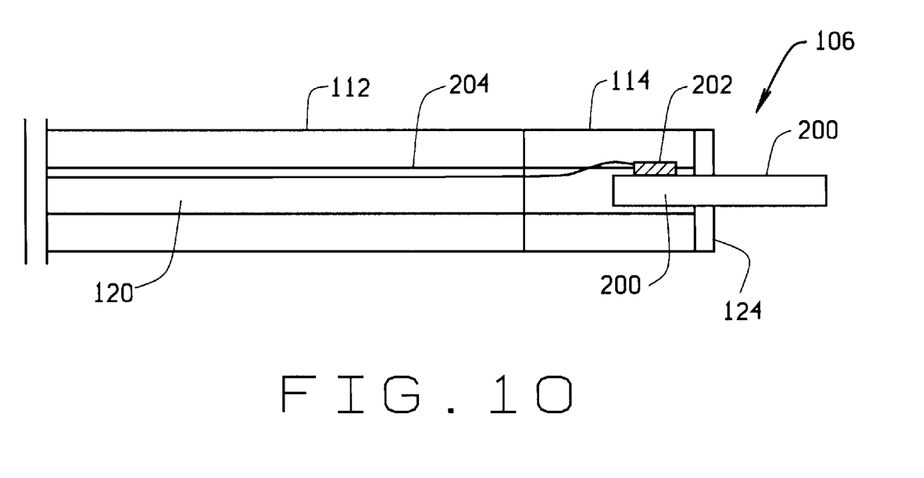
FIG. 10 is a schematic illustration of an alternative embodiment of the catheter distal end.

FIG. 10 is a schematic illustration of a first alternative embodiment of catheter distal end 106 showing central lumen 120 but, for clarity only, not showing control wires 108 and 110 or lumens 116 and 118. In this embodiment, a short piece of hypodermic tubing 300, such as nitinol or stainless steel tubing, is coupled to catheter distal end 106 and extends partially into lumen 120. In use, a guide wire (not shown) thus extends through tubing 300. A PZT crystal 302 is coupled to tubing 300 and further electrically coupled by a lead to an RF generator (not shown). Energy supplied to PZT crystal 302 by the RF generator causes high frequency vibration in PZT crystal 302, thus imparting lateral movement to tubing 300. The vibration is also imparted to the guide wire passing through tubing 300 due the close physical proximity of tubing 300 to the wire, and also due the presence of a liquid medium (blood or other body fluid) which acts as a coupling agent. As the catheter and guide wire are advanced, the lateral movement of tubing 300 and the guide wire act to enlarge the passageway along a path of least resistance through the vessel. The frequency of vibration of the PZT crystal is variable so that a resonant frequency of the system can be determined to maximize the advancement of catheter 100 and the guide wire.

Figure 11:
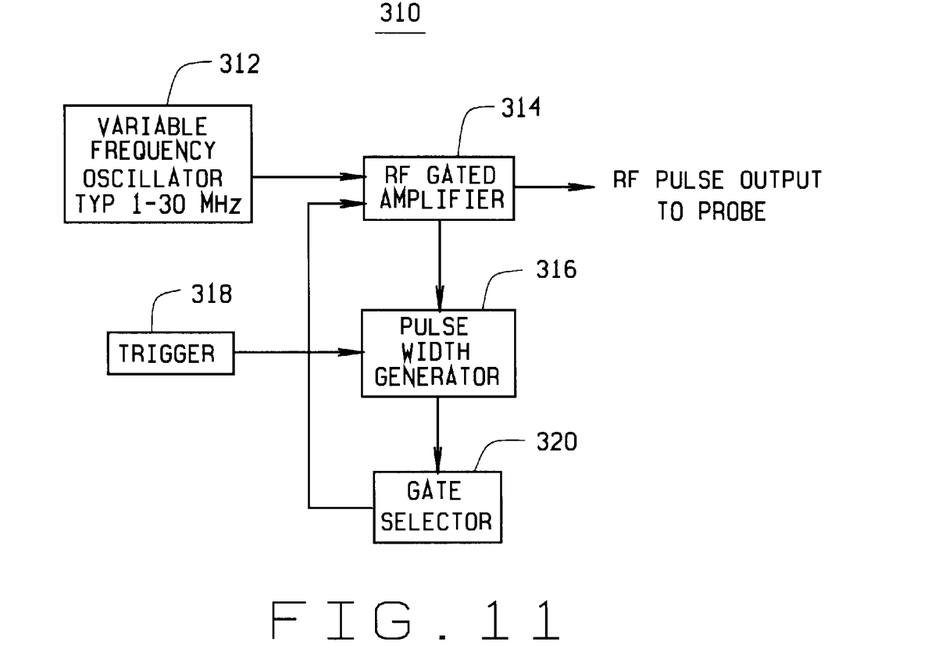
FIG. 11 is a block diagram of a system for exciting a PZT crystal in the guide wire advancement mechanism of FIG. 9.

FIG. 11 is a block diagram showing a system 310 which, in one embodiment, is used to excite PZT crystal 302. A variable frequency oscillator 312 is coupled to a gated amplifier 314. A pulse width generator 316 controlled by a trigger circuit 318 operates a gate selector 320 which in turn controls amplifier 314. The output of amplifier 314 provides a series of radio frequency pulses that are applied to PZT crystal 302.

In one embodiment, PZT crystal 302 has a broad bandwidth that is typically 2.5 to 4 times the nominal center frequency. In one embodiment, a single PZT crystal is used, but alternatively a second crystal is added, wherein the second PZT crystal has a nominal center frequency of about 2 to 3 times the first PZT crystal so that a wider frequency range is covered. Pulse width generator 316 is frequency tunable and in one embodiment is a tone burst device that produces a select number of sinusoidal impulses having a select time duration, amplitude and number of impulses. The tone burst is produced by gated amplifier 314 or by a pulsed oscillator. In one embodiment, the excitation device produces single square waves of a select amplitude and duration, but in an alternative embodiment produces a single burst including multiple square waves. By selectively controlling the impulse characteristics of the signal supplied to PZT crystal 302, the PZT crystal is selectively operated at various narrow band frequencies that are within its overall frequency range.

Figure 12:
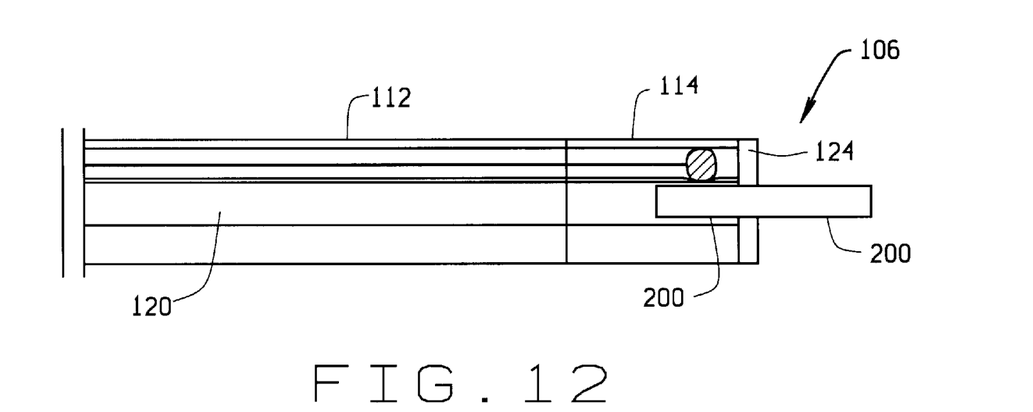
FIG. 12 is a schematic illustration of a second alternative embodiment of the catheter distal end.

FIG. 12 is a schematic illustration of a second alternative embodiment of catheter distal end 106, in which relatively low frequency vibration is coupled to tubing 300. In this embodiment, main catheter body 102 has a second central lumen 120, into which is inserted a rotating cam assembly 320 including a cam 322 on a speedometer type cable 324. Cam assembly 320 is coupled to a power source which imparts rotation to cam 306, which impinges upon tubing 300, thus causing tubing 300 to vibrate according to the rotational speed, size and shape of cam 306.

Figure 13:
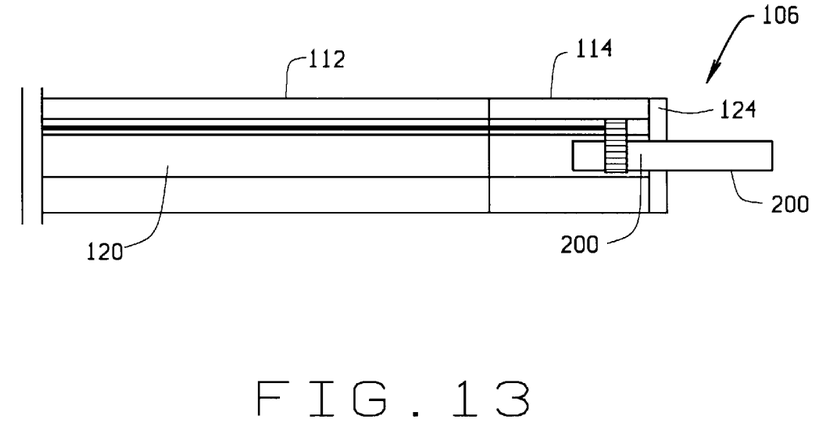
FIG. 13 is a schematic illustration of a third alternative embodiment of the catheter distal end.

FIG. 13 is a schematic illustration of a third alternative catheter distal end 106. Also in this embodiment, main catheter body 102 has a second central lumen 120, into which is inserted a speedometer type cable 310 terminating in a gear (not shown) which engages and rotates tubing 300 to produce a drill-like motion, which enlarges the passageway to facilitate passage of the catheter and guide wire.

Of course, alternative embodiments of catheter handle 132 include those embodiments which include either deflection mechanism 150 or advancement mechanism 152. In particular, an alternative embodiment o control handle 132 including advancement mechanism 152 but not deflection mechanism is especially suitable for use with catheters not having control wires.

In use, catheter 100 enhances the ability of a medical interventionist to control the movement of a variety of guide wires and to navigate a guide wire past difficult tissue such as total occlusions in a blood vessel. For example, a guide wire is loaded by inserting into lumen 120, extending out both proximal end 104 and distal end 106. The guide wire and catheter in combination are introduced into the body through an introducer sheath or guiding catheter, which are both commonly commercially available. A guide wire usually has some type of bend in its distal end to facilitate steering. The operator rotates the proximal end of the wire to align the bend of the guide wire to the direction in which advancement should occur. The operator then manually advances the guide wire through the vessel.

At times, the guide wire cannot be directed through the vessel in the desired direction. The path may be so tortuous that the wire does not rotate in the desired direction, or the end of the wire may not have a sufficient bend to achieve the desired direction. The catheter is then advanced over the wire such that distal end 106 of catheter body 102 is as close as possible to the distal end of the guide wire. The operator then adjusts the deflection of distal portion 114 by rotating knob 134 on control handle 132. The rotation moves, for example, control wire 108 distally while causing opposing control wire 110 to retract proximally, thus causing distal portion 114 to deflect relative to proximal portion 112. This establishes the new direction for the wire to be advanced. In one embodiment, distal portion 114 is radio-opaque to be visible under x-ray visualization so that the operator can see the direction of the deflection and the position of catheter body distal end 106 relative to the guide wire's distal end. Further, deflection mechanism 152 acts to lock distal portion 114 in a given deflected position until the operator changes the deflection by rotating knob 134.

During some procedures, such as trying to reanalyze a total occlusion in an artery, the guide wire reaches the barrier of the occlusion. At this point the operator uses the guide wire advancement mechanism to advance the guide wire very cautiously in incremental steps, trying to penetrate the occlusion to reach the lumen on the other side without perforating the normal artery wall. The lock is engaged in the handle to grip the wire. The ratcheting mechanism converts the "clicking" forward movement of control knob 134 to rotate the drive gear to the next incremental step. The locking mechanism holds the gear in place, while the handle resets by the retaining spring. The movement of the drive gear rotates the braking wheel to transfer the movement to the guide wire in a small step. The ratio of the gear wheel to the brake wheel serves as a transmission device to translate manual movement of the wire into incrementally advancing steps, and also to increase the forward force on the wire.

Some occlusions or lesions are so hard that the operator is unable to penetrate the barrier by force in the wire alone. A risk exists of pushing the wire sufficiently hard that the wire stores energy and then suddenly releases the energy by breaking through the hard layer or sliding to a softer spot in the barrier. When this happens, a sudden, uncontrolled movement of the wire can result, which often leads to complications such as a perforated artery. To address this problem, when a difficult lesion or tissue is encountered, the distal tip of catheter 100 is energized with a vibratory motion or rotating motion that is coupled to the hypodermic tubing at the distal end of the catheter to help penetrate the barrier.

This type of approach is implemented using the catheter with the PZT crystal, rotating cam or speedometer type cable coupled to the hypodermic tubing. With the PZT crystal or rotating cam, the vibration frequency can be varied from very low frequencies to ultrasonic frequencies depending on the type and response of the tissue being penetrated. The frequency can be adjusted to find a resonant frequency to further enhance the movement of the wire into the tissue.

While the invention has been described in terms of various specific embodiments, those skilled in the art will recognize that the invention can be practiced with modification within the spirit and scope of the claims.

What is claimed is:

1. A catheter for controlling the advancement of a guide wire extending therethrough, said catheter comprising:

a catheter body having a proximal end and a distal end, said catheter body comprising a distal portion coupled to a proximal portion, said distal portion more flexible than said proximal portion, said catheter body further having at least one central lumen therethrough configured to receive said guide wire, and a first side lumen and said second side lumen extending from the catheter body proximal end to the catheter body distal end and positioned on opposite sides of said catheter body; and said second side lumen extending from the catheter body proximal end to the catheter body distal end and positioned on opposite sides of said catheter body;

a first control wire extending from said catheter body proximal end to said catheter body distal end through said first side lumen, said first control wire coupled to said catheter body distal end; and a second control wire extending from said catheter body proximal end to said catheter body distal end through said second side lumen, said second control wire coupled to said catheter body distal end.

2. A catheter in accordance with claim 1 further comprising a control handle coupled to said catheter body proximal end, said control handle comprising a deflection mechanism coupled to said first control wire and said second control wire.

3. A catheter in accordance with claim 2 wherein said first control wire has a proximal end, said second control wire has a proximal end, said first control wire proximal end and said second control wire proximal end coupled to said deflection mechanism.

4. A catheter in accordance with claim 3 wherein said control handle further comprises a knob rotatably coupled to said deflection mechanism, said deflection mechanism configured to translate rotation of said knob to opposing movement of said first control wire and said second control wire.

5. A catheter in accordance with claim 4 wherein said deflection mechanism comprises a yoked mechanism for translating rotation of said knob to opposing movement of said first control wire and said second control wire.

6. A catheter in accordance with claim 5 wherein said deflection mechanism comprises:

a control cylinder coupled to said knob, said control cylinder having a central bore therethrough, a first side slot therethrough and a second side slot therethrough, said first side slot and said second side slot on opposing sides of said first cylindrical member and oriented at opposing angles relative to the long axis of said handle;

a chassis having a cylindrical portion, said cylindrical portion slidably engaged within the central bore of said control cylinder, said chassis cylindrical portion having a first side slot and a second side slot on opposing sides of said cylindrical portion, said first side slot and said second side slot extending substantially parallel to the long axis of said control handle, said cylindrical portion inserted into said control cylinder central bore so that said control cylinder first side slot and said cylindrical portion first side slot are in partial alignment so that a first movable opening is formed, and said control cylinder second side slot and said cylindrical portion second side slot are in partial alignment so that a second movable opening is formed.

7. A catheter in accordance with claim 6 said deflection mechanism further comprises:
a first dowel pin, said first dowel pin inserted through said first movable opening and coupled to said first guide pin; and
a second dowel pin, said second dowel pin inserted through said second movable opening and coupled to said second guide pin.

8. A catheter in accordance with claim 5 wherein said deflection mechanism comprises:
a first guide pin coupled to said first control wire; and
a second guide pin coupled to said second control wire, wherein said yoked mechanism is configured to produce opposing movement of said first guide pin and said second guide pin along a long axis of the control handle.

9. A catheter in accordance with claim 1 further comprising hypodermic tubing coupled to said catheter distal end, said hypodermic tubing having a central lumen in alignment with said catheter central lumen.

10. A catheter in accordance with claim 9 further comprising a vibration mechanism for vibrating said hypodermic tubing.

11. A catheter in accordance with claim 10 wherein said vibration mechanism comprises a PZT crystal coupled to said hypodermic tubing, said PZT crystal further coupled to an RF generator for exciting said PZT crystal.

12. A catheter in accordance with claim 10 wherein said catheter body has a first and a second central lumen therethrough, said vibration mechanism comprising a rotating cam inserted through said second central lumen and positioned to impinge on said hypodermic tubing.

13. A catheter in accordance with claim 9 wherein said catheter body has a first and a second central lumen therethrough, said catheter further comprising a speedometer type cable coupled to a gear, said cable and gear inserted through said second central lumen, said cable coupled to said hypodermic tubing and configured to rotate said hypodermic tubing.

14. A catheter in accordance with claim 1 further comprising a guide wire advancement mechanism coupled to said catheter body, said guide wire advancement mechanism configured to incrementally advance a guide wire through said catheter central lumen.

15. A catheter in accordance with claim 14, said guide wire advancement mechanism comprising:
a spring assembly block having a guide wire guiding channel therethrough;
a friction wheel positioned to contact a guide wire inserted through said guide wire guiding channel; and
at least one geared drive wheel coupled to said friction wheel.

16. A catheter in accordance with claim 15, said guide wire advancement mechanism further comprising:
a first spring element coupled to a housing portion;
a first ratchet element coupled to said first spring element and in reversible engagement with said at least one geared drive wheel;
a second spring element extending from said housing and contacting said spring block assembly; and
a second ratchet element coupled to said housing and in reversible engagement with said at least one geared drive wheel.

17. A catheter in accordance with claim 15, said guide wire advancement mechanism further comprising a roller bearing, said roller bearing positioned to contact the guide wire inserted through said guide wire guiding channel, said roller bearing further positioned so that the guide wire moves between said roller bearing and said friction wheel.

18. A catheter in accordance with claim 1 wherein said first control wire and said second control wire are continuous at said catheter body distal end, said first control wire and said second control wire forming a loop at said catheter distal end, said loop coupled to said catheter distal end.

19. A catheter in accordance with claim 18 further comprising a cap coupled to said catheter distal end, said cap having a central opening therethrough, said central opening aligned with said catheter central lumen, wherein said cap covers said loop.

20. A catheter in accordance with claim 1 wherein said distal portion is adjustable to a plurality of positions relative to said proximal portion.

21. A catheter in accordance with claim 19 wherein said cap comprises a radio-opaque material.

22. A catheter in accordance with claim 1 wherein said distal portion comprises a radio-opaque material.

23. A catheter in accordance with claim 1 further comprising hypodermic tubing extending through said catheter body proximal portion, through said first side lumen and said second side lumen.

24. A catheter in accordance with claim 1 wherein said catheter body has one central lumen therethrough.

25. A catheter for steering a guide wire extending therethrough, said catheter comprising:
a catheter body having a proximal end and a distal end, said catheter body comprising a distal portion and a proximal portion, said distal portion more flexible than said proximal portion, said catheter body having at least one central lumen extending from said catheter body proximal end to said catheter body distal end, said central lumen configured to receive said guide wire, and a first side lumen and a second side lumen extending from said catheter body proximal end to said catheter body distal end, said first side lumen and said second side lumen positioned on opposing sides of said catheter body;
a control wire comprising a first portion, a second portion and a loop portion disposed between said first portion and said second portion, said first portion extending through said first side lumen from said catheter body proximal end to said catheter body distal end, said second portion extending through said second side lumen from said catheter body proximal end to said catheter body distal end, said loop portion coupled to said catheter body distal end.

26. A catheter in accordance with claim 25 wherein said catheter body distal portion is adjustable to a plurality of positions relative to said proximal portion by selectively applying tension to said control wire first portion and said control wire second portion so that said control wire first portion and said control wire second portion move in opposing directions along the length of said catheter body.

27. A catheter in accordance with claim 26 further comprising a deflection mechanism coupled to said catheter body proximal end for selectively applying tension to said control wire first portion and said control wire second portion.

28. A catheter in accordance with claim 27 wherein said deflection mechanism comprises a yoked assembly coupled to said control wire, said yoked assembly configured to translate rotation of a control knob to opposing motion of said control wire first portion and said control wire second portion along the length of said catheter body.

* * * * *